United States Patent [19]
Yang et al.

[11] Patent Number: 5,734,037
[45] Date of Patent: *Mar. 31, 1998

[54] DNA ENCODING THE HUMAN CYTOKINE, INTERLEUKIN-9

[75] Inventors: Yu-Chung Yang, Indianapolis, Ind.; Agnes Brennan Ciarletta, Haverhill, Mass.; Susan Teresa Ricciardi, Randolph, Mass.; Steven C. Clark, Winchester, Mass.; Robert E. Donahue, Shirley, Mass.

[73] Assignee: Ludwig Institute for Cancer Research, New York, N.Y.

[*] Notice: The term of this patent shall not extend beyond the expiration date of Pat. No. 5,580,753.

[21] Appl. No.: 647,169

[22] Filed: May 9, 1996

Related U.S. Application Data

[60] Division of Ser. No. 515,308, Apr. 27, 1990, Pat. No. 5,580,753, which is a continuation-in-part of Ser. No. 356,033, May 23, 1989, abandoned.

[51] Int. Cl.⁶ .......................... C12N 15/24; C07K 14/54

[52] U.S. Cl. .............. 536/23.5; 536/24.3; 536/24.31; 435/71.1; 435/71.2; 435/172.3; 435/252.3; 435/320.1; 435/325; 435/366

[58] Field of Search .................. 536/23.1, 23.5, 536/24.3, 24.31; 435/69.52, 172.3, 240.2, 252.3, 320.1, 70.1, 71.1, 71.2, 325, 366; 530/351; 935/4, 11, 22, 66, 70, 72

[56] References Cited

U.S. PATENT DOCUMENTS 5,580,753  12/1996  Yang et al. ................. 435/69.5

OTHER PUBLICATIONS

The Cytokine Factsbook (1994) Callard & Gearing, Academic Press Inc. San Diego, CA 92101, pp. 79–80.

*Primary Examiner*—John Ulm
*Assistant Examiner*—Prema Mertz
*Attorney, Agent, or Firm*—Felfe & Lynch

[57] ABSTRACT

This invention provides a novel human erythropoietic growth factor and processes for producing it by recombinant DNA genetic engineering techniques.

8 Claims, 1 Drawing Sheet

FIG. 1

```
                    19                                              40
GAGCTC CGCTGTCAAG  ATG CTT CTG GCC ATG GTC CTT ACC TCT GCC
                   Met Leu Leu Ala Met Val Leu Thr Ser Ala

70
CTG CTC CTG TGC TCC GTG GCA GGC CAG GGG TGT CCA ACC TTG
Leu Leu Leu Cys Ser Val Ala Gly Gln Gly Cys Pro Thr Leu 100                                      130
GCG GGG ATC CTG GAC ATC AAC TTC CTC ATC AAC AAG ATG CAG
Ala Gly Ile Leu Asp Ile Asn Phe Leu Ile Asn Lys Met Gln

160
GAA GAT CCA GCT TCC AAG TGC CAC TGC AGT GCT AAT GTG ACC
Glu Asp Pro Ala Ser Lys Cys His Cys Ser Ala Asn Val Thr

190
AGT TGT CTC TGT TTG GGC ATT CCC TCT GAC AAC TGC ACC AGA
Ser Cys Leu Cys Leu Gly Ile Pro Ser Asp Asn Cys Thr Arg 220                                  250
CCA TGC TTC AGT GAG AGA CTG TCT CAG ATG ACC AAT ACC ACC
Pro Cys Phe Ser Glu Arg Leu Ser Gln Met Thr Asn Thr Thr

280
ATG CAA ACA AGA TAC CCA CTG ATT TTC AGT CGG GTG AAA AAA
Met Gln Thr Arg Tyr Pro Leu Ile Phe Ser Arg Val Lys Lys 310                                          340
TCA GTT GAA GTA CTA AAG AAC AAC AAG TGT CCA TAT TTT TCC
Ser Val Glu Val Leu Lys Asn Asn Lys Cys Pro Tyr Phe Ser

370
TGT GAA CAG CCA TGC AAC CAA ACC ACG GCA GGC AAC GCG CTG
Cys Glu Gln Pro Cys Asn Gln Thr Thr Ala Gly Asn Ala Leu

400
ACA TTT CTG AAG AGT CTT CTG GAA ATT TTC CAG AAA GAA AAG
Thr Phe Leu Lys Ser Leu Leu Glu Ile Phe Gln Lys Glu Lys 430                                  460
ATG AGA GGG ATG AGA GGC AAG ATA TGAAGATGAA ATATTATTTA
Met Arg Gly Met Arg Gly Lys Ile 490                                      520
TCCTATTTAT TAAATTTAAA AAGCTTTCTC TTTAAGTTGC TACAATTTAA

550
AAATCAAGTA AGCTACTCTA AATCAGTATC AGTTGTGATT ATTTGTTTAA 580                                  610
CATTGTATGT CTTTATTTTG AAATAAATAC ATATGTGGAA AAAAAAAAA

632
AAAAAAAAAA GCTC
```

DNA ENCODING THE HUMAN CYTOKINE, INTERLEUKIN-9

This is a division of application Ser. No. 07/515,308, filed Apr. 27, 1990, now U.S. Pat. No. 5,580,753, which is a continuation-in-part of application Ser. No. 07/356,033 filed on May 23, 1989 now abandoned.

The present invention relates to a novel cytokine that is capable of stimulating hematopoiesis, particularly erythroid colony development in the hematopoietic system and in stimulating the immune response, and to processes for obtaining the purified factor by recombinant genetic engineering techniques.

BACKGROUND OF THE INVENTION

A growing family of regulatory proteins that deliver signals between cells of the hematopoietic and immune systems has been identified. These regulatory molecules are known as cytokines. Many of the cytokines have been found to control the growth, development and biological activities of cells of the hematopoietic and immune systems. These regulatory molecules include all of the colony-stimulating factors (GM-CSF, G-CSF, M-CSF, and multi CSF or interleukin-3), the interleukins (IL-1 through IL-10), the interferons (alpha, beta and gamma), the tumor necrosis factors (alpha and beta), erythropoietin and leukemia inhibitory factor (LIF). These cytokines exhibit a wide range of biologic activities with target cells from bone marrow, peripheral blood, fetal liver, and other lymphoid or hematopoietic organs. See, e.g., G. Wong and S. Clark, *Immunology Today*, 9(5):137 (1988).

The biochemical and biological identification and characterization of certain cytokines was hampered by the small quantities of the naturally occurring factors available from natural sources, e.g., blood and urine. Many of the cytokines have recently been molecularly cloned, heterologously expressed and purified to homogeneity. [D. Metcalf, "The Molecular Biology and Functions of the Granulocyte-Macrophage Colony Stimulating Factors," *Blood*, 67(2) :257–267 (1986).]Among these cytokines are gamma interferon, human and murine GM-CSF, human G-CSF, human CSF-1 and human and murine IL-3. Several of these purified factors have been found to demonstrate regulatory effects on the hematopoietic and immune systems in vivo, including GM-CSF, MIP, M-CSF, G-CSF, IL-3, IL-2, IL-1, IL-7, IL-6, LIF, TNF, gamma-interferon, and erythropoietin.

Recently a new murine T cell growth factor, designated P40, was reported by J. Van Snick et al, *J. Exp. Med.*, 169:363–368 (1989).

The generation of erythrocytes from bone marrow or peripheral blood progenitor cells is a complex process that is supported in culture by several different hematopoietic growth factors. Erythropoietin (Epo), the primary regulator of the levels of circulating erythrocytes in vivo is absolutely required in culture to support the final stages of erythroid development including hemoglobinization. The growth and development of earlier erythroid progenitors, known as erythroid burst forming units (BFU-E) can be supported by several different cytokines including interleukin 3 (IL-3), granulocyte-macrophage colony-stimulating factor (GM-CSF) and, at least in the mouse system, IL-4 [See, R. Donahue et al, *Blood*, 66:1479 (1985); C. Sieff et al, *Science*, 230:1171 (1985); Y. Yang et al, *Cell*, 47:3 (1986); S. Emerson et al, *J. Clin. Invest.*, 82:1282 (1988); S. Emerson et al, *Blood*, 74:49 (1989); D. Rennick, *Proc. Natl. Acad. Sci.*, 84:6889 (1987) [Rennick I]; D. Rennick, *Blood*, 73:1828 (1989) [Rennick II]]. However, each of these cytokines interacts with several different hematopoietic cell lineages and none of them is specific in supporting erythropoiesis.

There remains a need in the art for additional proteins purified from their natural sources or otherwise produced in purified form, which are capable of stimulating hematopoiesis, specifically erythroid development, or enhancing immune responsiveness and are suitable for pharmaceutical use.

BRIEF SUMMARY OF THE INVENTION

In one aspect the present invention provides a novel human cytokine called IL-9, which is substantially free from association with other mammalian proteins. This biologically active novel factor is characterized by containing all or a portion of the same or substantially the same DNA and amino acid sequences reported below in Table I.

IL-9 is further characterized by an apparent molecular weight of between approximately 20 to 30 kd as determined by sodium dodecyl sulfate polyacrylamide gel electrophoresis under reducing conditions. The IL-9 factor of this invention has displayed biological activity in the MO7E assay, which indicates its involvement in regulating hematopoiesis. IL-9 in combination with Epo also displays biological activity in selectively supporting the proliferation of erythroid progenitor cells when tested in clonal culture systems with either peripheral blood, cord blood, or bone marrow target cells. Thus IL-9 is a cytokine with the potential to serve as a regulator in both the lymphoid and hematopoietic systems. IL-9 preferentially supports the development of a relatively early BFU-E population. In addition, IL-9 alone supports the growth of some mixed colonies. IL-9's responsiveness in these cultures indicates its role in stimulating an early progenitor cell population prior to the determination of erythroid committment. This IL-9 responsiveness is selectively retained at least through the early stages of erythroid development.

Another aspect of the invention includes DNA sequences comprising DNA sequences coding on expression for a human IL-9 polypeptide. One such DNA sequence is the same or substantially the same as the approximately 630 base nucleotide sequence which appears below in Table I, or fragments thereof.

Also provided by the present invention are vectors containing a DNA sequence encoding IL-9 in operative association with an expression control sequence. Host cells transformed with such vectors for use in producing recombinant IL-9 are also provided by the present invention.

The vectors and transformed cells of the invention are employed in another aspect, a novel process for producing recombinant human IL-9 polypeptide. In this process a cell line is transformed with a DNA sequence encoding IL-9. The IL-9 DNA sequence is in operative association with an expression control sequence in the cell. The transformed cell is then cultured. This claimed process may employ a number of known cells as host cells for expression of the polypeptide. Presently preferred cell lines are mammalian cell lines and bacterial cells.

Another aspect of this invention provides pharmaceutical compositions containing a therapeutically effective amount of IL-9 or a fragment thereof. These pharmaceutical compositions may be employed in methods for treating disease states or disorders characterized by red blood cell deficiencies. Additionally this factor may be employed as a general immune system stimulatory agent, e.g., to aid in T cell deficiencies.

A further aspect of the invention, therefore, is a method for treating such disorders, diseases, tissue injuries and the like by administering to a patient a therapeutically effective amount of IL-9 or an active fragment thereof in a suitable pharmaceutical carrier. These therapeutic methods may include administering simultaneously or sequentially with IL-9 polypeptides an effective amount of at least one other cytokine, hematopoietin, interleukin, growth factor, or antibody.

Still another aspect of the present invention are antibodies directed against IL-9. These antibodies are developed by employing IL-9 or a fragment thereof as an immunogenic substance in conventional methods for preparing monoclonal antibodies. Thus anti-IL-9 antibodies may be employed as diagnostic or therapeutic agents.

Other aspects and advantages of the present invention will be apparent upon consideration of the following detailed description of preferred embodiments thereof.

BRIEF DESCRIPTION OF THE FIGURE

FIG. 1 presents a cDNA sequence which encodes human IL-9, and the amino acid sequence of the protein.

DETAILED DESCRIPTION OF THE INVENTION

The present invention provides a biologically active human lymphokine, IL-9, substantially free of association with other mammalian proteinaceous materials. This protein may be produced in a variety of ways, including via recombinant DNA techniques to enable large scale production of pure, active IL-9 useful for therapeutic applications.

The active human IL-9 of this invention is characterized by the same or substantially the same approximately 144 amino acid protein sequence, as illustrated in Table I below. Recombinant human IL-9 of this invention, as expressed in mammalian cells, is also characterized by an apparent molecular weight of between 20 to 30 kd as determined by sodium dodecylsulfate polyacrylamide gel electrophoresis (SDS-PAGE) under reducing conditions. This size heterogeneity is a common feature of many glycoproteins which results from variations in the extent of carbohydrate modification.

The DNA sequence of Table I contains approximately 630 nucleotides, with approximately 450 nucleotides in the proper reading frame for the protein. IL-9 was originally cloned from a cDNA library prepared from mRNA of the human T lymphoblast cell line, C5MJ2, described in A. G. Leary et al, *Blood*, 69(3):953–956 (1987), according to the expression cloning method. IL-9 may also be produced by other human cell lines.

The expression cloning method has been previously described in G. G. Wong et al, *Science*, 228:810–815 (1985); Y. C. Yang et al, *Cell*, 47:3–10 (1986); and A. E. Namen et al, *Nature*, 333:571–573 (1988). Briefly, according to the expression cloning technique, the library was constructed in an expression vector pXM which permits the expression of cDNA inserts in mammalian cells, e.g. COS-1 cells. Screening of the library was performed by transfecting COS-1 cells with pools of cDNA clones. By assaying the supernatant fluid for IL-9 activity, cDNA clones expressing IL-9 activity were identified.

mRNA from several cell sources was examined for the ability to hybridize with a selected IL-9 cDNA clone. Northern blot analysis revealed that the T cell lines, C5MJ2 and C10MJ2, as well as lectin-stimulated human peripheral blood lymphocytes (PBL) synthesized readily detectable levels of mRNA that hybridized with the IL-9 clone.

One positive clone, which was isolated from a library of 250,000 clones, was sequenced. The IL-9 cDNA sequence from this clone, with the approximately 144 amino acid sequence encoded thereby, is shown in Table I below.

TABLE I

```
                          91                                    40
GAGCTC  CGCTGTCAAG  ATG  CTT  CTG  GCC  ATG  GTC  CTT  ACC  TCT  GCC
                    Met  Leu  Leu  Ala  Met  Val  Leu  Thr  Ser  Ala
                                   70

CTG  CTC  CTG  TGC  TCC  GTG  GCA  GGC  CAG  GGG  TGT  CCA  ACC  TTG
Leu  Leu  Leu  Cys  Ser  Val  Ala  Gly  Gln  Gly  Cys  Pro  Thr  Leu
               100                                                130

GCG  GGG  ATC  CTG  GAC  ATC  AAC  TTC  CTC  ATC  AAC  AAG  ATG  CAG
Ala  Gly  Ile  Leu  Asp  Ile  Asn  Phe  Leu  Ile  Asn  Lys  Met  Gln
                                             160

GAA  GAT  CCA  GCT  TCC  AAG  TGC  CAC  TGC  AGT  GCT  AAT  GTG  ACC
Glu  Asp  Pro  Ala  Ser  Lys  Cys  His  Cys  Ser  Ala  Asn  Val  Thr
                         190

AGT  TGT  CTC  TGT  TTG  GGC  ATT  CCC  TCT  GAC  AAC  TGC  ACC  AGA
Ser  Cys  Leu  Cys  Leu  Gly  Ile  Pro  Ser  Asp  Asn  Cys  Thr  Arg
     220                                             250

CCA  TGC  TTC  AGT  GAG  AGA  CTG  TCT  CAG  ATG  ACC  AAT  ACC  ACC
Pro  Cys  Phe  Ser  Gly  Arg  Leu  Ser  Gly  Met  Thr  Asn  Thr  Thr
                                   280

ATG  CAA  ACA  AGA  TAC  CCA  CTG  ATT  TTC  AGT  CGG  GTG  AAA  AAA
Met  Gln  Thr  Arg  Tyr  Pro  Leu  Ile  Phe  Ser  Arg  Val  Lys  Lys
               310                                                340

TCA  GTT  GAA  GTA  CTA  AAG  AAC  AAC  AAG  TGT  CCA  TAT  TTT  TCC
Ser  Val  Glu  Val  Leu  Lys  Asn  Asn  Lys  Cys  Pro  Tyr  Phe  Ser
                                        370

TGT  GAA  CAG  CCA  TGC  AAC  CAA  ACC  ACG  GCA  GGC  MC   GCG  CTG
Cys  Glu  Gln  Pro  Cys  Asn  Gln  Thr  Thr  Ala  Gly  Asn  Ala  Leu
                         400

ACA  TTT  CTG  AAG  AGT  CTT  CTG  GAA  ATT  TTC  CAG  AAA  GAA  AAG
Thr  Phe  Leu  Lys  Ser  Leu  Leu  Glu  Ile  Phe  Gln  Lys  Glu  Lys
     430                                             460
```

TABLE I-continued

| ATG | AGA | GGG | ATG | AGA | GGC | AAG | ATA | TGAAGATGAA | ATATTATTTA |
|-----|-----|-----|-----|-----|-----|-----|-----|------------|------------|
| Met | Arg | Gly | Met | Arg | Gly | Lys | Ile | | |
| | | | | | 490 | | | | 520 |
| TCCTATTTAT | TAAATTTAAA | | AAGCTTTCTC | | TTTAAGTTGC | | TACAATTTAA | | |
| | | | | | 550 | | | | |
| AAATCAAGTA | AGCTACTCTA | | AATCAGTATC | | AGTTGTGATT | | ATTTGTTTAA | | |
| | 580 | | | | | | 610 | | |
| CATTGTATGT | CTTTATTTTG | | AAATAAATAC | | ATATGTGGAA | | AAAAAAAAAA | | |
| | 632 | | | | | | | | |
| AAAAAAAAAA | GCTC | | | | | | | | |

The cDNA sequence of Table I contains a long open reading frame of 432 nucleotides, beginning with an ATG codon at nucleotides 17–19. The ATG is followed by 143 codons and a TGA termination triplet at nucleotides 449–451. The 432 nucleotides encode a 144 amino acid polypeptide with a calculated molecular mass of 16,000.

Similar to many secreted proteins, the DNA sequence of Table I for IL-9 contains a stretch of hydrophobic amino acids that resemble conventional secretory leader sequences [D. Perlman et al, *J. Mol. Biol.*, 67:391–409 (1983)], at the N-terminus. This very hydrophobic sequence is characteristic of a protein signal peptide and suggests that the mechanism of IL-9 secretion is that of typical secretory proteins.

The cDNA sequence for IL-9 also encodes three potential asparagine-linked glycosylation sites at amino acids 50–52 (Asn-Val-Thr); 63–65 (Asn-Cys-Thr); and 78–80 (Asn-Thr-Thr)[see, e.g., R. J. Winzler, "The Chemistry of Glycoproteins in Hormonal Proteins and Peptides", Vol. 1, C. H. Li, ed. Academic Press, New York, pp. 1 (1973)]. The IL-9 DNA sequence encodes eleven cysteine residues, located at amino acid positions 14, 21, 45, 47, 54, 56, 64, 68, 104, 109 and 113.

The nucleotide sequence of this IL-9 cDNA of the invention has been compared with the nucleotide sequences recorded in Genbank. The only factor with which IL-9 is believed to share significant sequence similarity is murine P40 [See, Van Snicket al, cited above]. Thus human IL-9 of this invention is immunologically distinct from other known human factors and proteins. The IL-9 factor may also be sufficiently different from murine factor P40 to be immunologically distinct therefrom.

The cDNA sequences of the present invention encode biologically active human IL-9, based on detection of the functional polypeptides produced by mammalian cells. One cloned sequence in plasmid pC5.22-3 was deposited with the American Type Culture Collection, 12301 Parklawn Drive, Rockville, Md. on May 23, 1989 under ATCC Accession No. 67988.

Allelic variations of the DNA sequence of Table I encoding the IL-9 factor described above are also included in the present invention, as well as analogs or derivatives thereof. Thus the present invention also encompasses these novel DNA sequences, free of association with DNA sequences encoding other primate proteins, and coding on expression for IL-9 polypeptides. These DNA sequences include those sequences which hybridize under stringent hybridization conditions [see, T. Maniatis et al, *Molecular Cloning (A Laboratory Manual)*, Cold Spring Harbor Laboratory (198), pages 387 to 389] to the DNA sequence of Table I. An example of one such stringent hybridization condition is hybridization in 4×SSC at 65° C., followed by a washing 0.1×SSC at 65° C. for thirty minutes. Alternatively an exemplary stringent hybridization condition is in 50% formamide, 4×SSC at 42° C.

DNA sequences, other than that of the murine P40, which hybridize to the sequence for IL-9 under relaxed hybridization conditions and which code on expression for IL-9 peptides having IL-9 biological properties also encode novel IL-9 polypeptides. Example of such non-stringent hybridization conditions are 4×SSC at 50° C. or hybridization with 30–40% formamide at 42° C. For example, a DNA sequence which shares regions of significant homology, e.g., sites of glycosylation or disulfide linkages, with the sequences of IL-9 and encodes a protein having one or more IL-9 biological properties clearly encodes a IL-9 polypeptide even if such a DNA sequence would not stringently hybridize to the IL-9 sequence of Table I.

Similarly, DNA sequences which code for C5 polypeptides but which differ in codon sequence due to the degeneracies of the genetic code or allelic variations (naturally-occurring base changes in the species population which may or may not result in an amino acid change) are also encompassed by this invention. Variations in the DNA sequence of C5 which are caused by point mutations or by induced modifications to enhance the activity, half-life or production of the polypeptides encoded thereby are also encompassed in the invention.

C5 polypeptides may also be produced by known conventional chemical synthesis. Methods for constructing the polypeptides of the present invention by synthetic means are known to those of skill in the art. The synthetically-constructed C5 polypeptide sequences, by virtue of sharing primary, secondary, or tertiary structural and conformational characteristics with C5 polypeptides may possess C5 biological properties in common therewith. Thus, they may be employed as biologically active or immunological substitutes for natural, purified C5 polypeptides in therapeutic and immunological processes.

The IL-9 polypeptides provided herein also include factors encoded by sequences similar to those of purified recombinant IL-9 but into which modifications are naturally provided or deliberately engineered.

Modifications in the peptide or DNA sequences can be made by one skilled in the art using known techniques. Modifications of interest in the IL-9 sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to one skilled in the art. [See, e.g., U.S. Pat. No. 4,518,584.]

Other specific mutations of the sequence of the IL-9 polypeptide described herein may involve modifications of a glycosylation site. The absence of glycosylation or only partial glycosylation results from amino acid substitution or deletion at any asparagine-linked glycosylation recognition site or at any site of the molecule that is modified by addition of O-linked carbohydrate. An asparagine-linked glycosylation recognition site comprises a tripeptide sequence which is specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Expression of such altered nucleotide sequences produces variants which are not glycosylated at that site.

Other analogs and derivatives of the sequence of C5 which would be expected to retain C5 activity in whole or in part may also be easily made by one of skill in the art given the disclosures herein. One such modification may be the attachment of polyethylene glycol (PEG) onto existing lysine residues, or the insertion of lysine residues into the sequence for attachment of PEG moieties. Such modifications are believed to be encompassed by this invention.

The present invention also provides a method for producing C5 polypeptides. The method of the present invention involves culturing a suitable cell or cell line, which has been transformed with a DNA sequence coding on expression for a IL-9 polypeptide or an active fragment thereof under the control of known regulatory sequences. Regulatory sequences include promoter fragments, terminator fragments and other suitable sequences which direct the expression of the protein in an appropriate host cell. Suitable cells or cell lines may be mammalian cells, such as Chinese hamster ovary cells (CHO) or 3T3 cells. The selection of suitable mammalian host cells and methods for transformation, culture, amplification, screening and, product production and purification are known in the art. See, e.g., Gething and Sambrook, *Nature,* 293:620–625 (1981), or alternatively, Kaufman et al, *Mol. Cell. Biol.,* 5(7) 1750–1759 (1985) or Howley et al, U.S. Pat. No. 4,419,446. Other suitable mammalian cell lines, are the monkey COS-1 cell line, and the CV-1 cell line. Mammalian cells are presently preferable for expression of the IL-9 factor due to the number of cysteine residues which indicate a possibly high degree of folding of this molecule.

Bacterial cells may also be useful as host cells suitable for the present invention, provided that the molecule produced therein retains activity in an unfolded or only partially or altered folded state, based on the differences in glycosylation resulting from expression of the factor in mammalian vs bacterial cells. Alternatively, the completely denatured IL-9 protein may be refolded and subjected to oxidation to generate refolded IL-9 molecules sufficiently similar to the native molecule to retain or mimic the biological activity of the native protein. For example, the various strains of *E. coli* (e.g., HB101, MC1061 and strains used in the following examples) are well-known as host cells in the field of biotechnology. Various strains of *B. subtilis,* Pseudomonas, other bacilli and the like may also be employed in this method.

Many strains of yeast cells known to those skilled in the art are also available as host cells for expression of the polypeptides of the present invention. Additionally, where desired, insect cells may be utilized as host cells in the method of the present invention. See, e.g. Miller et al, *Genetic Engineering,* 8:277–298 (Plenum Press 1986) and references cited therein.

The present invention also provides vectors for use in the method of expression of novel IL-9 polypeptides. These vectors contain the novel IL-9 DNA sequences which code for IL-9 polypeptides of the invention. Vectors incorporating truncated or altered fragments of IL-9, allelic variants thereof, or modified sequences as described above are also embodiments of the present invention and useful in the production of IL-9 polypeptides. The vector employed in the method also contains selected regulatory sequences in operative association with the DNA coding sequences of the invention and capable of directing the replication and expression thereof in selected host cells. One vector which has been shown to express IL-9 well in COS cells and is described in the examples below is pXM [Y. C. Yang et al, *Cell,* 47:3–10 (1986)]. Another vector which has been shown to express IL-9 well in CHO cells and is described in the examples is pEMC2B1.

Thus IL-9, purified to homogeneity from cells sources or produced recombinantly or synthetically, may be used in a pharmaceutical preparation or formulation to regulate the functions of the hematopoietic or the immune system. Specifically, IL-9 may regulate erythropoiesis IL-9 thus has use in treating pathological states characterized by a deficiency in red blood cells. As a red blood cell stimulator, IL-9 may be administered to patients anticipating surgery to enhance the blood composition. It may be used therapeutically in conjunction with chemotherapy to stimulate production of erythroid precursors. For example, IL-9 may be employed in the treatment of beta thalassemia and sickle cell anemia alone, or in conjunction with other treatments, by preferentially increasing red cells expressing fetal hemoglobin. It may also be employed adjunctively in transfusions or erythropoietic cell deficiency following a bone marrow transplantation. IL-9 may also be employed in treating platelet deficiencies, to repair tissue damage and accelerate wound healing or to enhance host defense generally.

In its utility in stimulating host defense, IL-9 may be used to treat pathological states resulting from disease, exposure to radiation or drugs, and include for example, leukopenia, bacterial and viral infections, e.g., AIDS, anemia, B cell or T cell deficiencies including immune cell deficiencies. Therapeutic treatment of wounds and diseases with these IL-9 polypeptide compositions may avoid undesirable side effects caused by treatment with presently available drugs.

The polypeptides of the present invention may also be employed, alone or in combination with other pharmaceutical agents, cytokines, hematopoietins, interleukins, growth factors or antibodies in the treatment of wounds or disease states.

Other uses for these novel polypeptides or active fragments thereof are in the development of monoclonal and polyclonal antibodies. Such antibodies may be generated employing IL-9, a fragment thereof, or a modified or allelic version thereof as an antigen. By using standard methods for the development of such antibodies known to one of skill in the art, polyclonal or monoclonal antibodies are made which may be useful as diagnostic or therapeutic agents.

Therefore, as yet another aspect of the invention are therapeutic and diagnostic compositions for treating or diagnosing the conditions referred to above, and methods for their use.

Such compositions comprise a therapeutically effective amount of an IL-9 polypeptide, fragment, or modified version thereof according to the present invention in admixture with a pharmaceutically acceptable carrier. This composition can be systematically administered parenterally.

Alternatively, the composition may be administered intravenously. If desirable, the composition may be administered subcutaneously. When systematically administered, the therapeutic composition for use in this invention is in the form of a pyrogen-free, parenterally acceptable aqueous solution. For use in tissue healing, the IL-9 factor may be present in a formulation suitable for local or topical application. The preparation of such pharmaceutically acceptable protein solutions or formulations, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, the daily regimen should be in the range of 1–1000 micrograms of polypeptide or 50 to 5000 units (i.e., one unit per ml being the concentration of polypeptide which leads to half maximal stimulation in the MO7E described below) of polypeptide per kilogram of body weight.

The therapeutic method and compositions of the present invention may also include co-administration with other human factors. One particularly preferred factor for co-administration with IL-9 is erythropoietin, to selectively support erythrocytes rather than other hematopoietic lineages. Other exemplary cytokines or hematopoietins for such use include the known factors IL-1, IL-2, IL-3, IL-4, IL-6, IL-7, GM-CSF, G-CSF, M-CSF, MIF, Meg-CSF, CSF-1, and the interferons. Growth factors like B cell growth factor, B cell differentiation factor, or eosinophil differentiation factors may also prove useful in co-administration with IL-9. The dosage recited above would be adjusted to compensate for such additional components in the therapeutic composition. Progress of the treated patient can be monitored by conventional methods.

The following examples illustratively describe the cloning, expression and production of human IL-9 and other methods and products of the present invention. These examples are for illustration only and do not limit the scope of the present invention.

EXAMPLE 1
Isolation of mRNA and Construction of cDNA Library

A human T lymphoblastoid cell line, C5MJ2, was chosen as the source of RNA extraction. These HTLV I transformed T cells were originally obtained from a patient with a diagnosis of mycosis fungoides. Cells were grown according to the method described in Leary et al, cited above. Total RNA was extracted according to the method of Chirgwin et al, *Biochemistry*, 18:5294–5299 (1979) from C5MJ2 cells that have been stimulated with 0.1% phytohemagglutinin (PHA) and 5 ng/ml phorbol 12-myristate 13-acetate (PMA) for 24 hours.

mRNA was prepared by oligo(dT)-cellulose chromatography [H. Aviv et al, *Proc. Natl. Aced. Sci. USA*, 69:1408–1412 (1972)]. Five micrograms of mRNA was used to synthesize double-stranded cDNA as described by Wong et al, cited above, with DNA polymerase I and RNase H in the second strand reaction [T. Maniatis et al, cited above]. The double-stranded DNA was blunted and ligated to synthetic semi-Xho adapters [Yang et al, *Cell*, 47:3–10 (1986)].

The COS-1 cell expression vector pXM [Y. C. Yang et al, cited above] was linearized at the unique Xho I site, adapted and ligated to the semi-Xho adapted cDNA. The ligation reaction was used to transform competent *Escherichia coli* strain HB101 [Y. C. Yang et al, cited above] to generate a library of approximately 250,000 ampicillin-resistant colonies.

EXAMPLE 2
DNA Preparation and COS-1 Cell Transfection

The expression cloning system previously described by G. G. Wong et al, cited above, was employed to isolate a cDNA encoding the IL-9 activity as follows.

Bacterial colonies from the above-described cDNA library were replicated onto nitrocellulose filters. Colonies from each filter were scraped into L-broth and plasmid DNA was isolated by previously described methods [J. A. Meyers et al, *J. Bacteriol.*, 127:1529–1536 (1976)]. Each primary DNA sample was prepared from a pool of 200–500 colonies.

Five micrograms of each plasmid DNA was used to transfect COS-1 cells by DEAE-dextran-mediated DNA transfection, with the addition of a 0.1 mM chloroquine treatment [L. M Sompayrac et al, *Proc. Natl. Acad. Sci. USA*, 78:7575–7578 (1981) and H. Luthman et al, *Nucl. Acids Res.*, 11:1295–3081. (1983)] Culture supernatant fluid from transfected COS-1 cells was harvested 72 hours after transfection and assayed for IL-9 activity according to the MO7E assay described below in Example 6.

Plasmid DNA from the positive pools was re-transfected into COS-1 cells and transfected supernatants were re-screened for IL-9 activity. These samples were then subdivided to contain fewer clones until individual clones were isolated. Of the 550 supernatants for the initial COS-1 cell transfections of the primary pools, one sample showed the best overall IL-9 activity.

The pools with the highest IL-9 activity were selected and subdivided to contain fewer clones, their DNAs were prepared, transfected, and the transfected supernatants were examined for IL-9 activity until single clones expressing IL-9 activity were obtained.

One clone which consistently demonstrated the best IL-9 activity was re-examined in the MO7E assay of Example 6. The IL-9 activity of this clone was also compared with other cytokines (IL-3, GM-CSF, IL-1α, IL-1β, IL-6, LIF, Lymphotoxin and IL4).

EXAMPLE 3
Protein Analysis

The polypeptide encoded by the cDNA of pC5.22-3 was identified using pulse-labeling experiments. Forty-eight hours after chloroquine treatment, culture supernatant from COS-1 cells transfected with recombinant DNA of IL-9-positive clones was removed and cells were pulse-labelled with 0.5 mCi [35S]methionine in 0.5 ml of DMEM for 4 hours at 37° C. Radiolabelled supernatant was collected and subjected to a 12% SDS-PAGE [U. K. Laemmli, *Nature*, 227:680–685 (1970)]. After electrophoresis, the gel was immersed in a fluorography enhancing solution (Enhance; New England Nuclear, Boston, Mass.), dried, and exposed to X-ray film.

This analysis of proteins secreted by COS-1 cell transfected with pC5.22-3 DNA revealed the presence of a 20–30 kd polypeptide which was absent in a mock transfected control.

EXAMPLE 4
RNA Blot Analysis

Five micrograms of mRNA from PHA/PMA-stimulated or unstimulated C5MJ2 cells, C10MJ2 cells, PHA/PMA-stimulated human PBL, was electrophoresed through 1.2% agarose gel containing 2.2M formaldehyde [H. Lehrach et al, *Biochemistry*, 16:4743 (1977)]. The formaldehyde-denatured RNA was transferred to nylon filter (Zetabind; Cuno, Meriden, Conn.), as described [E. M. Southern, *J. Mol. Biol.*, 98:503–517 (1975)].

The cDNA probe was made by cleaving cDNA inserts from the vector with Xho I restriction enzyme and labelling the inserts with $^{32}$P using random oligonucleotides as primers in the presence of the large fragment of DNA polymerase I [A. P. Feinberg et al, *Analy. Biochemistry*, 132:6–13 (1983)]. The nylon filter was prehybridized for 4 hours at 65° C. and hybridized with $^{32}$P-labelled cDNA probe in hybridization solution consisting of 4× SSC, 0.5% SDS, 5×Denhardt's solution and 100 ug/ml denatured salmon sperm DNA for 16 hours at 65° C.

After hybridization, the filter was washed two times with 2× SSC/0.1% SDS for 30 minutes at 65° C. and then with 0.2× SC/0.1% SDS for 30 minutes at 65° C. The filter was then dried and applied to X-ray film.

This RNA blot analysis revealed that the T-cell lines, C5MJ2 and C10MJ2, as well as lectin-stimulated human PBL, synthesized readily detectable levels of a 0.8 kb mRNA that hybridized with the IL-9 clone.

EXAMPLE 5
DNA Sequence Analysis

The nucleotide sequence of the cDNA clone of pC5.22-3 was determined as described [G. G. Wong et al and Y. C. Yang et al, cited above] by generating ordered sets of overlapping fragments via Bal 31 nuclease digestion and subcloning into M13 vectors [M. Poncz et al, *Proc. Natl. Acad. Sci. USA*, 79:4298–4302 (1982); and J. Messing et al, *Gene*, 19:269–276 (1982)]. Single-stranded DNA was prepared, and the nucleotide sequence was determined by the dideoxynucleotide chain-termination procedure [F. Sanger et al, *Proc. Natl. Acad. Sci. USA*, 74:5463–5467 (1977)].

EXAMPLE 6
M07E Cell Assay for IL-9

The M07E cell line was derived from the peripheral blood of an infant with acute megakarocytic leukemia [G. C. Avanzi et al, *Brit. J. Haematol.*, 69:359–366 (1988)]. Growth of M07E cells is dependent on the presence in the medium of GM-CSF or IL3.

M07E cells are grown in the presence of recombinant human IL-3 at an approximate concentration of 8 units per milliliter. The assay is performed essentially as follows: Two to four days following passage, the M07E cells are removed from culture, washed once, counted and set aside.

100 ul of the media [heat inactiviated fetal calf serum (HIFCS)/Dulbecco's Modified Eagles medium (DME) with penstrep (PS) and glutamine] containing the material to be assayed is plated in each well of a microtiter plate. The cells prepared above are spun down and resuspended at a concentration of 1–2×10$^5$ cells/ml in 10% HIFCS/DME+PS+ glutamine. 100 microliters of cells are plated in each well and incubated with samples in the presence or absence of anti-human GMCSF or anti-IL-6 antibodies at 37° C. in 10% CO$_2$ for 72 hours. Thereafter 0.5 uCi $^3$H-thymidine is added per well and the wells are incubated for 4 hours at 37° C. Cells are harvested using an automatic cell harvester onto GFC Type C filter paper (LKB), washed with ethanol and dried. Filters are then immersed in scintillation fluid and counted for $^3$H uptake.

The conditioned medium from C5MJ2 cells provided a higher level of stimulation in the M07E assay than could be accounted for by the cytokines known to be produced by these cells. This was confirmed using anti-GM-CSF, anti-IL-3 and anti-IL-6 antibodies with the C5MJ2 cell supernatant. The residual incorporation in this experiment indicated the existence of the novel "IL-9" factor and provided the bioassay for expression cloning of this factor.

Based on the thymidine uptake measurement, the IL-9 protein is active in this assay in stimulating the proliferation of leukemic blast cells. This activity was not neutralized by exposure to antibodies to the known lymphockines which are also active in this assay, indicating that IL-9 acts directly as a mitogen for the cells and not through induction of known factors.

EXAMPLE 7
Expression of Recombinant Human IL-9

To produce IL-9, the cDNA encoding it is transferred into an appropriate expression vector, of which numerous types are known in the art for mammalian, insect, yeast, fungal and bacterial expression, by standard molecular biology techniques.

One such vector for mammalian cells is pXM [Y. C. Yang et al, *Cell*, 47:3–10 (1986)]. This vector contains the SV40 origin of replication and enhancer, the adenovirus major late promoter, a cDNA copy of the adenovirus tripartite leader sequence, a small hybrid intervening sequence, an SV40 polyadenylation signal and the adenovirus VA I gene, in appropriate relationships to direct the high level expression of the desired cDNA in mammalian cells [See,. e.g., Kaufman, *Proc. Natl. Acad. Sci. USA*, 82:689–693 (1985)]. The pXM vector is linearized with the endonuclease enzyme XhoI and subsequently ligated in equimolar amount separately to the cDNA encoding IL-9 that was previously modified by addition of synthetic oligonucleotides that generate Xho I complementary ends to generate constructs for expression.

Another vector for mammalian expression is pEMC2B1. This vector may be derived from pMT2pc which has been deposited with the American Type Culture Collection (ATCC), Rockville, Md. (U.S.A.) under Accession Number ATCC 40348. The DNA is linearized by digestion of the plasmid with PstI. The DNA is then blunted using T$_4$ DNA polymerase. An oligonucleotide 5' TGCAGGCGAGCCT-GAA TTCCTCGA 3' is then ligated into the DNA, recreating the PstI site at the 5' end and adding an EcoRI site and XhoI site before the ATG of the DHFR cDNA. This plasmid is called pMT21. pMT21 is cut with EcoRI and XhoI which cleaves the plasmid at two adjacent cloning sites. An EMCV fragment of 508 base pairs was cut from pMT$_2$ECAT$_1$ [S. K. Jong et al, *J. Virol.*, 62:1651–1660 (1989)] with the restriction enzymes EcoRi and TaqαI. A pair of oligonucleotides 68 nucleotides in length were synthesized to duplicate the EMCV sequence up to the ATG. The ATG was changed to an ATT, and a C is added, creating a XhoI site at the 3' end. A TaqαI site is situated at the 5' end. The sequences of the oligonucleotides were: 5' CGAGGT-TAAAAAACGTCTAGGCCCCCCGAAC-CACGGGGACGTGGTTTTCCTTT GAAAAACACGAT-TGC 3' and its complementary strand.

Ligation of the pMT21 EcoRI-to-XhoI fragment to the EMCV EcoRI-to-TaqαI fragment and to the TaqαI/XhoI oligonucleotides produced the vector pEMC2B1. This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells. The EMC2B1 vector is linearized with the endonuclease enzyme EcoRI and subsequently ligated in equimolar amount separately to the cDNA encoding IL-9 that was previously modified by addition of synthetic oligonucleotides that generate EcoRI complementary ends to generate constructs for expression. These constructs can be expressed in various hosts with appropriate vectors.

a. Mammalian Cell Expression

To obtain expression of the IL-9 protein for use in the assay described below, the pXM construct containing the cDNA for IL-9 is transfected into COS cells, as described in Example 5. Similarly the pEMC-2B1 construct containing the cDNA for IL-9 is transfected into CHO cells (see Example 8). The conditioned medium from the transfected COS cells contains IL-9 biological activity as measured in the M07E assay.

The mammalian cell expression vectors described herein may be synthesized by techniques well known to those skilled in this art. The components of the vectors, e.g. replicons, selection genes, enhancers, promoters, and the like, may be obtained from natural sources or synthesized by known procedures. See, Kaufman et al, *J. Mol. Biol.*, 159:511–521 (1982); and Kaufman, *Proc. Natl. Acad. Sci., USA*, 82:689–693 (1985). Exemplary mammalian host cells include particularly primate cell lines and rodent cell lines, including transformed cell lines. Normal diploid cells, cell strains derived from in vitro culture of primary tissue, as well as primary explants, are also suitable. Candidate cells need not be genotypically deficient in the selection gene so long as the selection gene is dominantly acting. For stable integration of the vector DNAs, and for subsequent amplification of the integrated vector DNAs, both by conventional methods, CHO cells may be employed. Alternatively, the vector DNA may include all or part of the bovine papilloma virus genome [Lusky et al, *Cell*, 36:391–401 (1984)], and be carried in cell lines such as C127 mouse cells as a stable episomal element. Other suitable mammalian cell lines include but are not limited to, HeLa, COS-1 monkey cells, mouse L-929 cells, 3T3 lines derived from Swiss, Balb-c or NIH mice, BHK or HaK hamster cell lines, Stable transformants are then screened for expression of the product by standard immunological, biological or enzymatic assays. The presence of the DNA and mRNA encoding the IL-9 polypeptides may be detected by standard procedures such as Southern blotting and RNA blotting. Transient expression of the DNA encoding the polypeptides during the several days after introduction of the expression vector DNA into suitable host cells, such as COS-1 monkey cells, is measured without selection by activity or immunologic assay of the proteins in the culture medium.

One skilled in the art can also construct other mammalian expression vectors comparable to the pXM vector by, e.g., inserting the DNA sequences of IL-9 from the plasmids with appropriate enzymes and employing well-known recombinant genetic engineering techniques and other known vectors, such as pJL3 and pJL4 [Gough et al., *EMBO J.*, 4:645–653 (1985)] and pMT2 (starting with pMT2-VWF, ATCC #67122; see PCT application PCT/US87/00033). The transformation of the vectors with IL-9 into appropriate host cells can result in expression of the IL-9 polypeptides.

b. Bacterial Expression Systems

Similarly, one skilled in the art could manipulate the sequences encoding IL-9 by eliminating any mammalian regulatory sequences flanking the coding sequences and inserting bacterial regulatory sequences to create bacterial vectors for intracellular or extracellular expression of IL-9 of the invention by bacterial cells. The DNA encoding IL-9 may be further modified to contain different codons to optimize bacterial expression as is known in the art. Preferably the sequence encoding the mature IL-9 is operatively linked in-frame to nucleotide sequences encoding a secretory leader polypeptide permitting bacterial expression, secretion and processing of the mature IL-9 polypeptide, also by methods known in the art. The expression of IL-9 in *E. coli* using such secretion systems may result in the secretion of an active polypeptide. Alternatively, if intracellular expression leads to production of a denatured and inactive IL-9 polypeptide, this species can be subjected to standard methods of protein refolding to yield active IL-9.

The compounds expressed through either route in bacterial host cells may then be recovered, purified, and/or characterized with respect to physicochemical, biochemical and/or clinical parameters, all by known methods.

c. Insect or Yeast Cell Expression

Similar manipulations can be performed for the construction of an insect vector for expression of IL-9 polypeptides in insect cells [See, e.g., procedures described in published European patent application 155,476].

Similarly yeast vectors are constructed employing yeast regulatory sequences to express the cDNA encoding IL-9 in yeast cells to yield secreted extracellular active IL-9. [See, e.g., procedures described in published PCT application WO 86/00639 and European patent application EP 123,289.]

EXAMPLE 8
Construction of CHO Cell Lines Expressing High Levels of IL-9

One method for producing high levels of the IL-9 protein of the invention from mammalian cells involves the construction of cells containing multiple copies of the cDNA encoding IL-9.

The cDNA is co-transfected with an amplifiable marker, e.g., the DHFR gene for which cells containing increasing concentrations of methotrexate (MTX) according to the procedures of Kaufman and Sharp, *J. Mol. Biol.,* (1982) supra. This approach can be employed with a number of different cell types. Alternatively, the IL-9 cDNA and drug resistance selection gene (e.g., DHFR) may be introduced into the same vector. A preferred vector for this approach is pEMC-2B1.

For example, the pEMC-2B vector containing the IL-9 gene in operative association with other plasmid sequences enabling expression thereof is introduced into DHFR-deficient CHO cells, DUKX-BII, by protoplast fusion and transfection. The IL-9 gene and DHFR marker gene are both efficiently expressed when IL-9 is introduced into pEMC2B1. DHER expressing transformants are selected for growth in alpha media with dialyzed fetal calf serum. Transformants are checked for expression of IL-9 by bioassay, immunoassay or RNA blotting and positive pools are subsequently selected for amplification by growth in increasing concentrations of MTX (sequential steps in 0.02, 0.2, 1.0 and 5uM MTX) as described in Kaufman et al., *Mol. Cell Biol.,* 5:1750 (1983). The amplified lines are cloned, and IL-9 protein expression is monitored by the IL-9 assay. IL-9 expression is expected to increase with increasing levels of MTX resistance.

In any of the expression systems described above, the resulting cell lines can be further amplified by appropriate drug selection, resulting cell lines recloned and the level of expression assessed using the IL-9 assay described herein.

EXAMPLE 9
Effect of IL-9 on Colony Formation by Peripheral Blood Progenitors Clonal assays were performed to assess the effect of IL-9 on progenitor cells of the hematopoietic system as follows.

a. Preparation of Cytokines and Antibodies

Recombinant human GM-CSF, IL-3, IL-6, granulocyte-colony-stimulating factor (G-CSF), and erythropoietin (Epo) were all purified proteins, having specific activies of $8.7\times10^6$, $3.9\times10^6$, $1\times10^6$, $2.0\times10^6$, and $1.5\times10^5$ units per mg of protein, respectively. Except for Epo, which was used at a final concentration of 2 U/m, these proteins were used in culture at a final concentration of 10 ng/ml. IL-4, IL-9, leukemia-inhibitory factor (LIF), and IL1α were conditioned media from COS-1 cells that were transfected with the appropriate cDNA. These transfection supernatants had half-maximal activities of $1.3\times10^4$, $6\times10^3$, $1\times10^5$, and $1.5\times10^3$, respectively. IL-1α was used in culture at a concentration of 5 U/ml. The other transfection supernatants were used at a final dilution of 1:100.

To neutralize-endogenous GM-CSF production by contaminating lymphocytes or monocytes, a 1:100 final dilution of sheep heteroantiserum directed against GM-CSF (Genetics Institute, Cambridge, Mass.) was added directly to the cultures. This concentration of antibody is capable of completely neutralizing 90 U in this assay system.

b. Cell Preparation—Peripheral Blood

Residual leukocytes were obtained as a byproduct from platletpheresis of healthy donors using a Fenwal CS-3000 blood separator. Peripheral blood derived progenitors were isolated from cold aggregated monocytes prepared as described initially by Mentzer et al, *Cell Immunol.*, 101:101 (1986) using the mononuclear cells of these residual leukocytes. The aggregated cells were gently disrupted and the monocytes removed magnetically by a magnetic particle concentrator (Dynal, Great Neck, N.Y.) after they had been allowed to phagocytize iron particles (Lymphocyte Separator Reagent, Technicon, Tarrytown, N.Y.) at 37° C. for 45 minutes. The remaining cells were allowed to adhere to plastic dishes for 1–2 hours to further remove contaminating monocytes. These cells were used for routine clonal cultures at cell densities of $1$–$2\times10^4$/ml. Under these conditions, the cell preparation typically yielded a BFU-E plating efficiency of 118 per $10^5$ cells when plated in IL-3 plus erythropoietin. Few, if any granulocyte/macrophage colonies were obtained. More highly purified progenitor populations were prepared by positive immuno-magnetic selection for the early hematopoietic cell surface marker CD34+. This methodology has previously been described [T. Lea et al, *Scand. J. Immunol.*, 22:207 (1985)]. Positive selection for CD34 progenitors was performed using the commercially available HPCA-1 antibody purchased from Becton-Dickinson (Mountainview, Calif.). This highly purified cell preparation was used in clonal assays at concentrations between 100 and 250 cells/ml and typically yielded a BFU-E plating efficiency of about 50% in the presence of IL-3.

c. Clonal Assay Cultures

Enriched progenitor cells were cultured in 0.9% methylcellulose in IMDM with 30% FCS, 0.9% deionized bovine serum albumin (Sigma Fraction V), and $10^{-4}$M 2-mercaptoethanol. One unit of recombinant erythropoietin (Genetics Institute, Cambridge, Mass.) was added to each 0.5 ml culture in a dropwise fashion on day 3. Red colonies containing typically >1000 cells were scored as BFU-E 12–14 days after the initiation of triplicate cultures.

For initial studies with IL-9, erythroid progenitors isolated from the leukocytes obtained as a by-product of plateletpheresis were utilized. In the purification of the erythroid progenitors, these cells were observed to selectively aggregate along with monocytes when peripheral mononuclear cells are incubated at 4° C.

The aggregated progenitors were further fractionated and used as target cells in standard erythroid methylcellulose cultures in the presence of Epo. In addition to IL-3 and GM-CSF, IL-9 proved to be effective in supporting the formation of erythroid bursts (BFU-E), while G-CSF, IL-1α, IL-4, IL-6, and LIF all were not (Table II). In this culture system, IL-9 yielded 40–50% as many BFU-E as did either IL-3 or GM-CSF. The erythroid burst promoting activity (BPA) of IL-9 was not blocked by addition of neutralizing antiserum against GM-CSF, the most abundantly produced BPA by accessory cells in these cultures, indicating that IL-9 acts directly on erythroid progenitors. IL-3 alone yielded the highest frequency of BFU-E formation and this level was not augmented by addition of either IL-9 or GM-CSF, indicating that the IL-9 and GM-CSF each interact with subsets of IL-3-responsive erythroid progenitors. Most of the BFU-E supported by IL-9 were of the diffuse, late-hemoglobinizing morphology, indicating a possible interaction with a relatively early subpopulation of IL-3-responsive progenitors.

The peripheral blood progenitors were further purified through immuno-magnetic bead selection for CD34+ cells to study whether IL-9 acts indirectly or directly with erythroid progenitors. When plated in the presence of IL-3 and Epo at concentrations of either 100 or 250 cells/ml, 46% of these cells yielded erythroid bursts (Table II). This same cell population revealed BFU-E plating efficiencies of approximately 20% in IL-9 and 42% in GM-CSF. Because of the high purity of these progenitors and the low density of plating, this result provides strong evidence that there is a subpopulation of BFU-E that responds directly to IL-9.

TABLE II

Peripheral Blood BFU-E Supported by Different Cytokines

| | BFU-E(Mean(SD)/$10^5$ cells) |
|---|---|
| A. Partially-purified progenitors | |
| medium alone | 3(5) |
| IL-1α | 7(6) |
| IL-3 | 62(16) |
| IL-4 | |
| IL-6 | 3(6) |
| IL-9 | 33(20) |
| GM-CSF | 76(27) |
| LIF | 7(6) |
| B. CD34 + progenitors | |
| medium alone | 4(2) |
| IL-3 | 46(4) |
| GM-CSF | 42(4) |
| IL-9 | 20(4) |

EXAMPLE 10

Effect of IL-9 on Colony Formation by Bone-Marrow and Cord Blood Progenitors

Because peripheral blood is a relatively poor source of granulocyte/macrophage (GM) progenitors, IL-9 was compared with IL-3 and GM-CSF for the ability to support colony formation by adult bone marrow-derived progenitors and by progenitors from human cord blood. Either of these sources, but especially bone marrow, have abundant levels of progenitors from all lineages and are more useful than peripheral blood for testing the lineage specificity of the different cytokines.

a. Cell Preparation—Bone Marrow

Bone marrow was collected by aspiration from normal adult volunteers in preservative-free heparin. Mononuclear cells were isolated by density centrifugation using Ficoll-Paque (Pharmacia, Piscataway, N.J.), and adherent cells removed by overnight adherence to 100×15-mm plastic tissue culture dishes (Corning, Corning, N.Y.) in Iscove's modified Dulbecco's medium (IMDM) with 20% fetal calf serum (FCS) at 37° C. under 5% $CO_2$. Clonal assays were plated at $2.5×10^4$ cells/ml.

b. Cell Preparation—Cord Blood

Umbilical cord blood was obtained from umbilical cord and placental tissues scheduled for discard under a protocol approved by the Brigham and Women's Hospital Human Investigations Committee. The cord blood was collected in preservative-free heparin, with the mononuclear cells isolated by centrifugation over Ficoll-Paque (Pharmacia, Piscataway, N.J.). Adherent cells were removed by overnight adherence to plastic tissue culture dishes. The resulting non-adherent fraction was plated in clonal assays at a cell concentration of $2.5×10^4$ cells/ml.

c. Results

As summarized in Table III, with either source of target cells, IL-9 largely supported BFU-E formation with occasional mixed (CFU-GEMM) colonies also observable. However, colonies from the later progenitors of the neutrophil and macrophage lineages (CFU-GM, CFU-M and CFU-G) were rarely observed in IL-9-supported cultures in contrast, IL-3 and GM-CSF yielded high levels of these colony types. IL-9 has also not displayed any activity tested alone or in combination with IL-3 in cultures of human and murine megakaryocyte progenitors. Thus, unlike IL-3 and GM-CSF which display activities with multiple hematopoietic lineages, IL-9 appears to be specific for erythroid development.

TABLE III

Comparison of Hematopoietic Lineage Specificities of Interleukin-3, Interleukin-9, and GM-CSF

|  | BFU-E | CFU-G/M | CFU-Mix |
|---|---|---|---|
|  | (Mean(SD)/$10^5$ cells) | | |
| A. Bone marrow progenitors | | | |
| Media alone | 92(17) | 171(35) | 29(11) |
| GM-CSF | 239(38) | 247(49) | 48(14) |
| IL-3 | 259(31) | 176(35) | 102(20) |

TABLE III-continued

Comparison of Hematopoietic Lineage Specificities of Interleukin-3, Interleukin-9, and GM-CSF

|  | BFU-E | CFU-G/M | CFU-Mix |
|---|---|---|---|
|  | (Mean(SD)/$10^5$ cells) | | |
| IL-9 | 175(29) | 121(18) | 45(16) |
| B. Cord blood | | | |
| Media alone | 35(26) | 21(12) | 5(5) |
| GM-CSF | 115(17) | 72(8) | 16(8) |
| IL-3 | 131(20) | 77(9) | 45(9) |
| IL-9 | 99(12) | 35(5) | 11(5) |

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. An isolated nucleic acid molecule which hybridizes to a nucleic acid molecule which has a nucleotide sequence that is complementary to the nucleotide sequence presented in Table 1, at 4× SSC at 65° C. or at 4× SSC with 50% formamide at 42° C.

2. Isolated nucleic acid molecule of claim 1, comprising cDNA.

3. Isolated nucleic acid molecule of claim 1, having the nucleotide sequence set forth in Table 1.

4. A plasmid which comprises the isolated nucleic acid molecule of claim 3 and a regulatory element operatively associated with said isolated nucleic acid molecule.

5. A cell of transformed with the plasmid of claim 4.

6. The cell of claim 5, wherein said cell is a humane cell or a bacterial cell.

7. A cell transformed with the isolated nucleic acid molecule of claim 3.

8. The cell of claim 7, wherein said cell is a mammalian cell or a bacterial cell.

* * * * *

UNITED STATES PATENT AND TRADEMARK OFFICE
CERTIFICATE OF CORRECTION

PATENT NO. : 5,734,037
DATED : Mar. 31, 1998
INVENTOR(S) : Yang et al.

It is certified that error appears in the above-identified patent and that said Letters Patent is hereby corrected as shown below:

In column 1, line 3, change "07,515,308" to -- 07/515,308 --.
In column 4, Table 1, in the seventh line of the righthandmost column, change "Gin" to
-- Gln --.
In column 4, Table 1, in the eighth line of the lefthandmost column, change "Giu" to
-- Glu --.
In column 5, line 31, change "Glyccproteins" to -- Glycoproteins --.
In column 5, line 42, "Snicket" should read –Snick et-.--.
In column 5, line 63, change "(198)" to -- (1982) --.

In column 7, line 39, after "5(7)" insert -- : --.
In column7, line 58, change "Pseudomonas" to -- *Pseudomonas* --.

UNITED STATES PATENT AND TRADEMARK OFFICE
CERTIFICATE OF CORRECTION

PATENT NO.    : 5,734,037
DATED         : Mar. 31, 1998
INVENTOR(S)   : Yang et al.

It is certified that error appears in the above-identified patent and that said Letters Patent is hereby corrected as shown below:

In column 9, line 56, change "Aced." to -- Acad. --.
In column 12, line 7, change "lymphockines" to -- lymphokines --.
In column 15, line 7, change "2 U/m" to -- 2U/ml --.
In column 15, line 9, change "IL1α" to -- IL-1α --.
In column 15, line 16, after "neutralize" delete -- -- --.
In column 15, Table II, in the third line of the right-hand column, change "62(16)" to -- 82(16) --.
In column 16, Table II, in the fourth line of the right-hand column, insert -- 7(6) --.
In Claim 5, column 18, line 36, after "cell" delete -- of --.
In Claim 6, column 18, line 37, change "humane" to -- human --.

Signed and Sealed this

Seventh Day of November, 2000

Attest:

Q. TODD DICKINSON

*Attesting Officer*          *Director of Patents and Trademarks*